(12) United States Patent
Greiner

(10) Patent No.: US 10,943,124 B2
(45) Date of Patent: Mar. 9, 2021

(54) MONITORING COMPLIANCE WITH MEDICAL PROTOCOLS BASED ON OCCLUSION OF LINE OF SIGHT

(71) Applicant: KONINKLIJKE PHILIPS N.V., Eindhoven (NL)

(72) Inventor: Harald Greiner, Nufringen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 243 days.

(21) Appl. No.: 16/083,949

(22) PCT Filed: Mar. 28, 2017

(86) PCT No.: PCT/EP2017/057242
§ 371 (c)(1),
(2) Date: Sep. 11, 2018

(87) PCT Pub. No.: WO2017/167708
PCT Pub. Date: Oct. 5, 2017

(65) Prior Publication Data
US 2020/0311432 A1    Oct. 1, 2020

(30) Foreign Application Priority Data
Apr. 1, 2016    (EP) .................................... 16163547

(51) Int. Cl.
*G06K 9/00* (2006.01)
*G16H 40/20* (2018.01)
(Continued)

(52) U.S. Cl.
CPC ........ *G06K 9/00718* (2013.01); *A61B 5/1176* (2013.01); *G06K 7/10722* (2013.01);
(Continued)

(58) Field of Classification Search
None
See application file for complete search history.

(56) References Cited

U.S. PATENT DOCUMENTS

| 8,289,392 | B2 | 10/2012 | Senior |
| 8,731,239 | B2 | 5/2014 | Gefen |
| 2010/0328443 | A1* | 12/2010 | Lynam .................. G06K 9/036 348/77 |

FOREIGN PATENT DOCUMENTS

| EP | 2892006 | 7/2015 |
| WO | 2014/062755 | 4/2014 |
| WO | 2014/074585 | 5/2014 |

* cited by examiner

*Primary Examiner* — Leon Flores

(57) ABSTRACT

In various embodiments, an image monitoring device (100) may acquire (200) video data that captures a medical room. Image processing may be performed on the acquired image data to perform the following tasks: identifying (202) at least one medical apparatus (402) in the medical room; identifying (204) a medical personnel in the medical room; detecting (206) that the medical personnel has occluded a line of sight between the image monitoring device and the at least one medical apparatus; and determining (206) an amount of time that the medical personnel occludes the line of sight. In various embodiments, the amount of time may be compared to one or more thresholds set forth by the first medical protocol. An alert may be triggered (208) in response to a determination that the amount of time fails to satisfy a first threshold of the one or more thresholds.

14 Claims, 6 Drawing Sheets

(51) Int. Cl.
  *A61B 5/1171* (2016.01)
  *G06K 7/10* (2006.01)
  *G06K 7/14* (2006.01)
  *G06K 9/46* (2006.01)
  *G08B 21/18* (2006.01)
(52) U.S. Cl.
  CPC ......... *G06K 7/1413* (2013.01); *G06K 7/1417* (2013.01); *G06K 9/00288* (2013.01); *G06K 9/00362* (2013.01); *G06K 9/00771* (2013.01); *G06K 9/46* (2013.01); *G08B 21/182* (2013.01); *G16H 40/20* (2018.01); *G06K 2209/01* (2013.01); *G06K 2209/057* (2013.01)

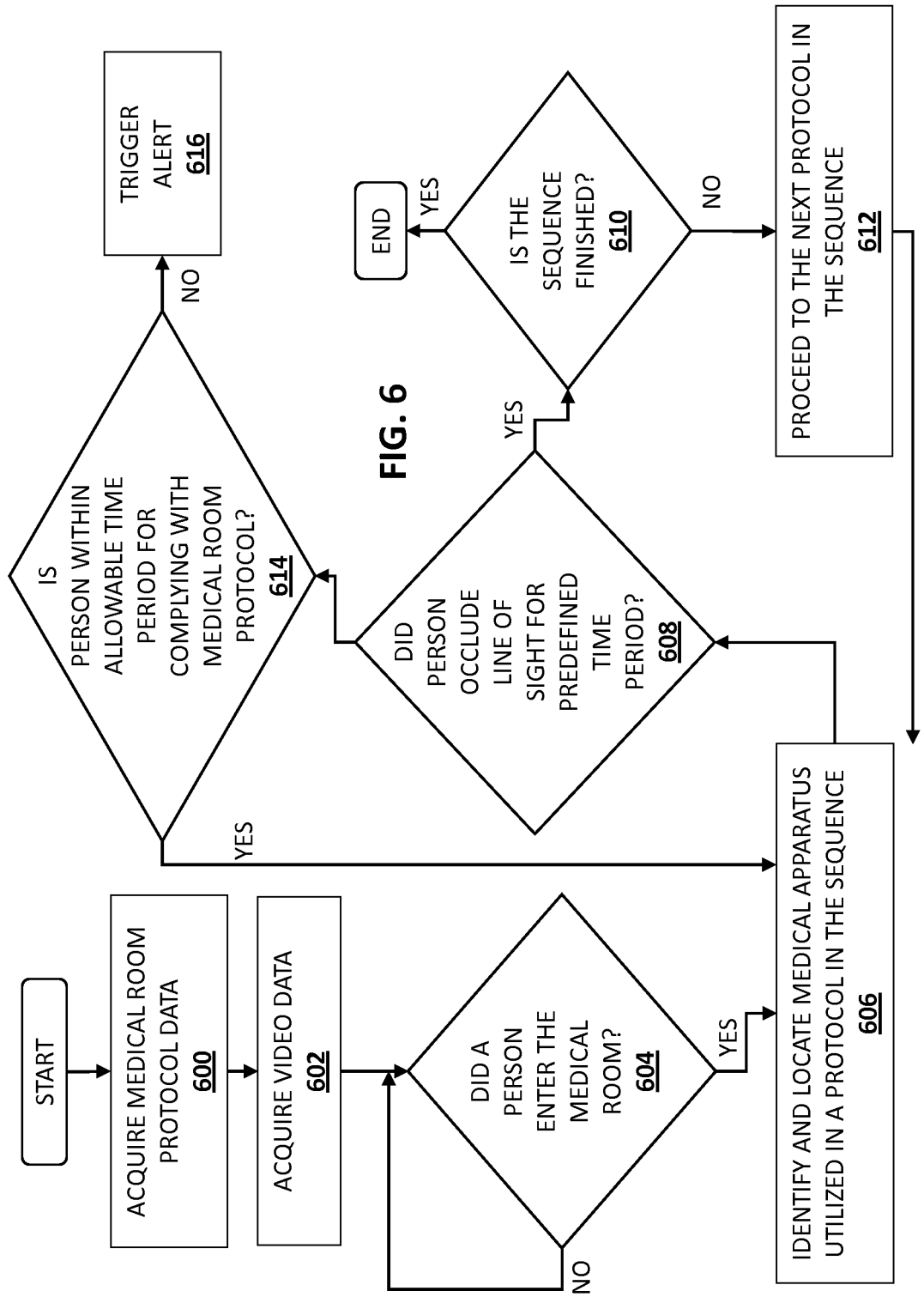

MONITORING COMPLIANCE WITH MEDICAL PROTOCOLS BASED ON OCCLUSION OF LINE OF SIGHT

CROSS REFERENCE TO RELATED APPLICATIONS

This application is the U.S. National Phase application under 35 U.S.C. § 371 of International Application No. PCT/EP2017/057242, filed Mar. 28, 2017, published as WO 2017/167708 on Oct. 5, 2017, which claims the benefit of European Patent Application Number 16163547.9 filed Apr. 1, 2016. These applications are hereby incorporated by reference herein.

BACKGROUND OF THE INVENTION

Medical care is provided in healthcare facilities such as hospitals, nursing homes, and clinics. While medical personnel go to great lengths to prevent the spread of infection, patients can regularly acquire infections when admitted in a healthcare facility. Some of these infections, such as *Clostridium difficile* (*C. Diff*), can be life threatening and difficult to treat. Transmission of infection typically is attributable to the failure of healthcare providers to comply with protocols. Accordingly, compliance of healthcare providers with protocols is of utmost importance to secure the health of their patients.

In many healthcare facilities, various types of imaging systems have been installed for monitoring purposes. They allow enhanced security and provide for a more responsive care, and they can be used with little disruption to the healthcare facility's environment. In one application, image processing techniques are used to track the movements of a healthcare provider while inside a room. One way to do this is by determining the occurrence of an occlusion in the field-of-view of the video camera.

U.S. Pat. No. 8,289,392 discloses a method of acquiring close-up views of objects of interest. The system tracks moving objects of interest by detecting occlusions of the objects of interest to static objects. U.S. Pat. No. 8,731,239 discloses a system of locating and identifying multiple moving objects that are undergoing persistent occlusions with each other.

BRIEF SUMMARY OF THE INVENTION

The present disclosure relates to a method comprising: acquiring, using an image monitoring device, video data that captures a medical room; performing image processing on the acquired video data to determine compliance with a first medical protocol, wherein the image processing includes: identifying at least one medical apparatus in the medical room; identifying a medical personnel in the medical room; detecting that the medical personnel has occluded a line of sight between the image monitoring device and the at least one medical apparatus; and determining an amount of time that the medical personnel occludes the line of sight, comparing the amount of time to one or more thresholds set forth by the first medical protocol; and triggering an alert in response to a determination that the amount of time fails to satisfy a first threshold of the one or more thresholds.

The present disclosure also relates to a system comprising: a medical room protocol database that stores medical room protocols; an image monitoring device to acquire video data that captures a medical room, and an alert system. The image monitoring device may perform image processing on the acquired video data to: identify at least one medical apparatus (402) in the medical room; identify a medical personnel in the medical room; detect that the medical personnel has occluded a line of sight between the image monitoring device and the at least one medical apparatus; and determine an amount of time that the medical personnel occludes the line of sight. The alert system may trigger an alert when the medical personnel occludes a line of sight between the image monitoring device and an at least one medical apparatus for an amount of time that fails to satisfy at least one medical room protocol stored in the medical room protocol database.

BRIEF DESCRIPTION OF THE DRAWINGS

The accompanying drawings, which are included to provide a further understanding of the disclosure, are incorporated herein to illustrate embodiments of the disclosure. Along with the description, they also serve to explain the principle of the disclosure. In the drawings:

FIG. 6 illustrates a flowchart according to yet another embodiment of the present disclosure wherein the detected health care provider has to comply with multiple medical room protocols in a specific sequence.

DETAILED DESCRIPTION OF THE EMBODIMENTS

The following are definitions of terms as used in the various embodiments of the present disclosure.

The term "room" as used herein refers to a space enclosed by walls, a floor, and a ceiling that can be occupied by or populated with one or more people or objects. The term "medical room" as used herein refers to a room in a medical facility, such as a hospital. The medical room will typically comprise one or more hospital equipment, devices, and facilities, as well as patients, medical personnel, and/or visitors. The term "medical room protocol" as used herein is used to collectively refer to rules, procedures, actions, events, or tasks a healthcare provider must perform while inside a medical room.

The term "medical apparatus" as used herein refers to any equipment or facility used in order for a healthcare provider to comply with medical room protocols. Examples of medical apparatus include but are not limited to sinks, wash stations, operating table, surgery equipment (e.g., clamps, stents, scalpels, etc.), X-ray machines, stethoscopes, temperature measurement devices, dialysis machines, adjustable hospital beds, ultrasound equipment, magnetic resonance imaging ("MRI") equipment, physical therapy equipment, computerized tomography ("CT") equipment, infusion pumps, defibrillators, catheters, injection pens, and so forth.

"Image data" as used herein refers to lossy data (e.g., JPEG) or lossless data (e.g., bitmap) representing one or more images acquired by an electronic device such as a camera. "Image data" may refer to a single image and/or to a sequence of images (e.g., a video). "Video data" as used herein may refer to a lossy or lossless sequence of images or "frames." The term "occlusion of the line of sight" as used herein refers to an obstruction by a moving object to an image monitoring device's field of view to a static object.

The term "database" as used herein refers to a collection of data and information organized in such a way as to allow the data and information to be stored, retrieved, updated, and manipulated and to allow them to be presented into one or more formats such as in table form or to be grouped into text, numbers, images, and audio data. The term "database" as used herein may also refer to a portion of a larger database, which in this case forms a type of database within a database. "Database" as used herein also refers to conventional databases that may reside locally or that may be accessed from a remote location, e.g., remote network servers. The database typically resides in computer memory that includes various types of volatile and non-volatile computer memory. Memory that stores the database may include high-speed random access memory or non-volatile memory such as magnetic disk storage devices, optical storage devices, and flash memory. Memory that stores the database resides may also store one or more software for processing and organizing data received by and stored into the database.

Figure 1:
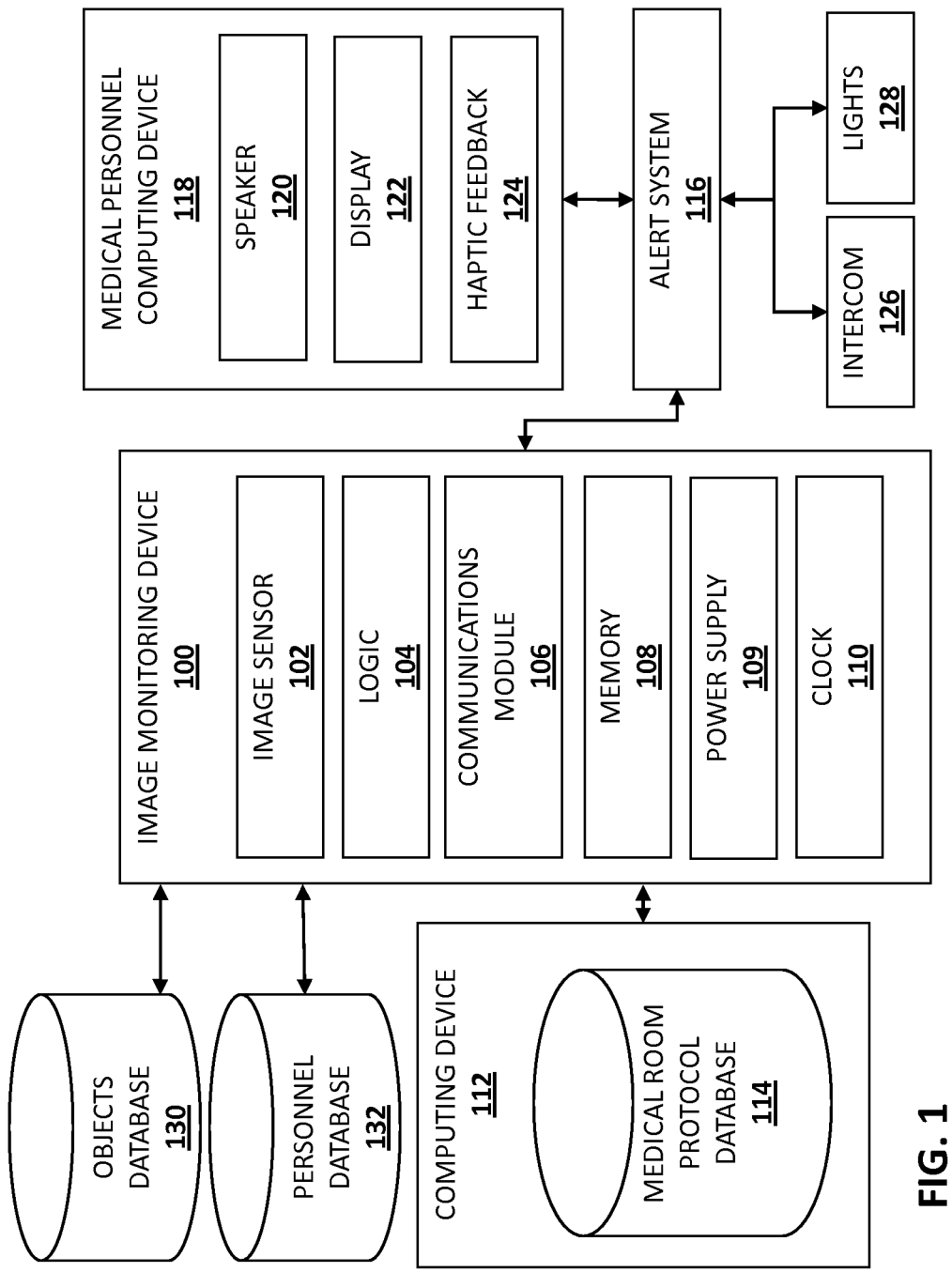
FIG. 1 illustrates a block diagram of a system for reinforcing medical room protocols according to an example embodiment of the present disclosure.

FIG. 1 schematically illustrates an example system for reinforcing medical room protocols, in accordance with various embodiments. As shown, an image monitoring device may include an image sensor 102, a logic 104, a communications module 106, a memory 108, a power source 109, and/or a clock 110. Alternatively, the image monitoring device may not include an image sensor and instead have an image input arranged to receive image sensor data (or video data) provided by an external camera (image) device, which includes an image sensor. Also, the image monitoring device 100 may be connected to (e.g., in network communication with) a computing device 112, an alert system 116, an objects database 130, and/or a personnel database 132.

The term "image monitoring device" as used herein refers to any device capable of capturing, recording, processing or storing an image, video, and other forms of digital or electronic representation of an object or a scene. An image sensor 102 may come in various forms in various embodiments. These types are well-known and are available commercially. Commonly used image sensors are semiconductor charged-coupled devices ("CCD") or active pixel sensors in complementary metal-oxide-semiconductor ("CMOS"). Examples of image monitoring devices 100 may include digital cameras, video cameras, CCTVs, webcams, smart cameras, smart phones, tablets, and so forth.

In accordance with the various aspects of the present disclosure, logic 104 is meant to be inclusive of one or more data processors, image processors, central processing units, or any variety of multi-core processing device. Some processors may execute instructions stored in memory 108 to perform various techniques described herein. Logic 104 may additionally or alternatively include one or more application-specific integrated circuits ("ASIC") and/or one or more field-programmable gate arrays ("FPGA").

The communications module 106 may be a standalone device or a component of another device that facilitates communication, e.g., sending and receiving of commands, triggers, notifications, prompts, acknowledgments, information, messages, forms, and various types of data such as video, text, and audio between, for example, the image monitoring device 100, the computing device 112, and/or the alert system 116. In accordance with various embodiments, the communications module 106 may include any transmitter or receiver used for Wi-Fi, Bluetooth, infrared, NFC, radio frequency, cellular communication, visible light communication, Li-Fi, WiMax, ZigBee, fiber optic and other forms of wireless communication devices. Alternatively, the communications module 106 may be a physical channel such as a USB cable, an Ethernet cable, or other wired forms of communication. In accordance with the various embodiments of the present disclosure, the memory 108 may include high-speed random access memory or non-volatile memory such as magnetic disk storage devices, optical storage devices, or flash memory. Memory 108 may also store software instructions for facilitating processes, features and applications of the system described herein.

In some embodiments, image monitoring device 100 may be a standalone device such as a "smart" video camera that includes most or all of the components depicted in FIG. 1 in a single housing. In other embodiments, components of image monitoring device 100 may be distributed across multiple housings. For example, in some embodiments, a video camera (i.e., image sensor 102) may be mounted on a wall, and may be connected wirelessly (e.g., using Bluetooth or Wi-Fi) or via one or more wires to another device (e.g., a small computing device) that houses logic 104 and other components depicted in FIG. 1. The small computing device that houses logic 104 may perform one or more techniques described herein. In yet other embodiments, image/video data acquired by image sensor 102 may be transmitted "in the raw", e.g., using communications module 106, to computing device 112. Computing device 112 may then perform various techniques described herein using the acquired image/video data.

The computing device 112 may have various form factors, such as a smartphone, a desktop, a laptop, a tablet, a set-top box, or any other device that includes various standard computing components (most not depicted in FIG. 1), such as one or more processors, one or more types of memory, at least one computer program or operating system, and a power supply. Furthermore, the computing device 112 may include a medical room protocol database 114. In various embodiments, the medical room protocol database 114 may be stored in local memory of the computing device 112. Alternatively, the medical room protocol database 114 may take the form of a stand-alone device connected to the computing device 112 through a cloud or a network (not depicted).

Medical room protocol database 114 may store data and pre-stored parameters corresponding to one or more protocols and/or rules for performing a medical procedure. For example, medical room protocol database 114 may store appropriate amounts of time for which particular actions should be performed (e.g., a doctor should scrub his or her hands for x minutes prior to performing some evaluation), expected order of operations for various medical procedures, expected operational parameters of medical equipment, etc. In some embodiments, medical room protocol database 114 may also store corresponding decisions and actions resulting from a comparison of those pre-stored data and parameters with detected, monitored, or measured one or more data and parameters.

In various embodiments, the alert system 116 may include one or more computing devices, each having standard computing components (not depicted, e.g., processors, memory, communication modules, power sources, etc.). The computing device(s) that form alert system 116 may be configured to generate and/or transmit alerts to various other computing devices, such as image monitoring device 100, computing device 112, or even computing devices 118 operated by individual medical personnel. A computing device 118 operated by a medical personnel such as a doctor or nurse may have various form factors, such as a smartphone, a desktop, a laptop, a tablet, a wearable computing device (e.g., a watch, glasses, arm band, etc.), a set-top box, or any other device that includes various standard computing components (not depicted in FIG. 1).

A computing device 118 operated by medical personnel may in various embodiments include one or more output devices through which the medical personnel can consume various alerts raised by alert system 116. For example, in FIG. 1, the computing device 118 operated by medical personnel includes a speaker 120, a display 122 (which may be a touchscreen in some instances), and a haptic feedback mechanism 124 (e.g., to cause the computing device 118 to vibrate). In other embodiments, alerts triggered by alert system 116 may cause output from other devices, such as an intercom system 126, one or more lights 128 affixed adjacent a door into a medical room, computing device 112, image monitoring device 100, and so forth.

In various embodiments, objects database 130 may store image data portraying medical devices, equipment, medical supplies, nonmedical devices, medical apparel, and/or other objects found in a medical setting or a patient room. Personnel database 132 may store medical personnel and patient information, including their photos, recorded voice data, and/or video data.

In accordance with the various aspects of the present disclosure, various medical apparatuses and persons may be detected and identified by the image sensor 102 using, for example, pattern recognition, image recognition, image registration, object recognition, facial recognition, feature extraction, color recognition, optical character recognition, motion analysis covering tasks such as egomotion, tracking, and optical flow, pose estimation, machine vision, machine learning, content-based image retrieval, shape recognition, artificial intelligence, neural networks, and other methods of image processing as well as other types of computer vision-based.

Figure 2:
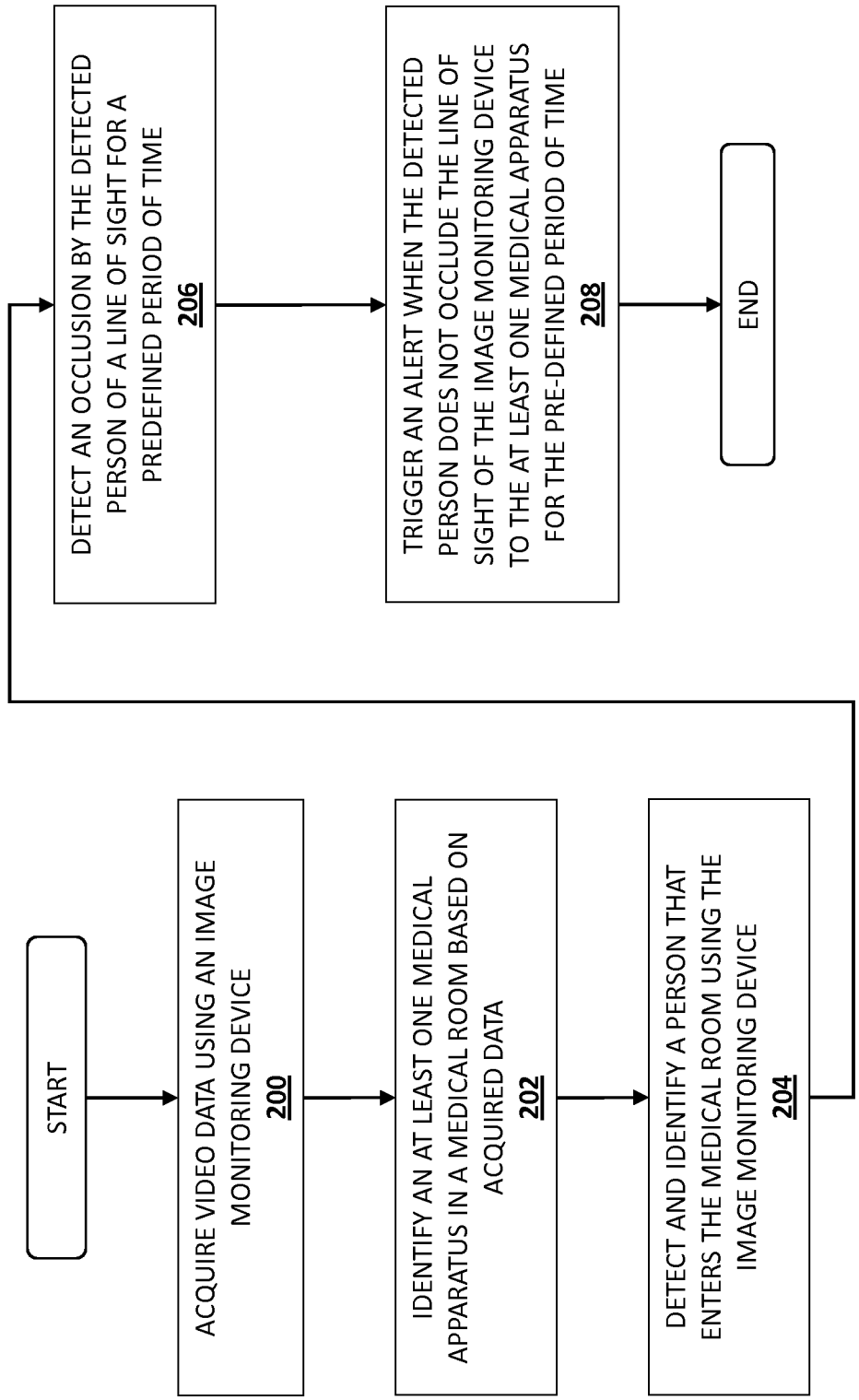
FIG. 2 illustrates a flowchart according to an example embodiment of the present disclosure.

FIG. 2 illustrates an example method of the present disclosure. At block 200, an image monitoring device 100 installed in a medical room may acquire video data. Alternatively, the image monitoring device may be arranged to receive acquire video data from an external image device installed in the medical room. Such an external image device can be for example a surveillance camera. At block 202, at least one medical apparatus may be identified based on analysis of the acquired video data (e.g., using object recognition based on records in objects database 130). At block 204, during the acquisition of video data, the system may continuously loop to determine if a person has entered the medical room. Once a person is detected, the image monitoring device 100 may identify the detected person (e.g., using facial recognition based on records in personnel database 132). Then, at block 206, the image monitoring device may determine if the detected person occludes the monitoring device line of sight to the at least one determined medical apparatus for a predefined period of time. Such an occlusion may indicate to the image monitoring device 100 that a medical room protocol is to be performed or being performed by the detected person. At block 208, an alert may be triggered if no occlusion of the monitoring device 100 line of sight to the at least one medical apparatus was detected for at least the pre-defined amount of time.

Figure 3:
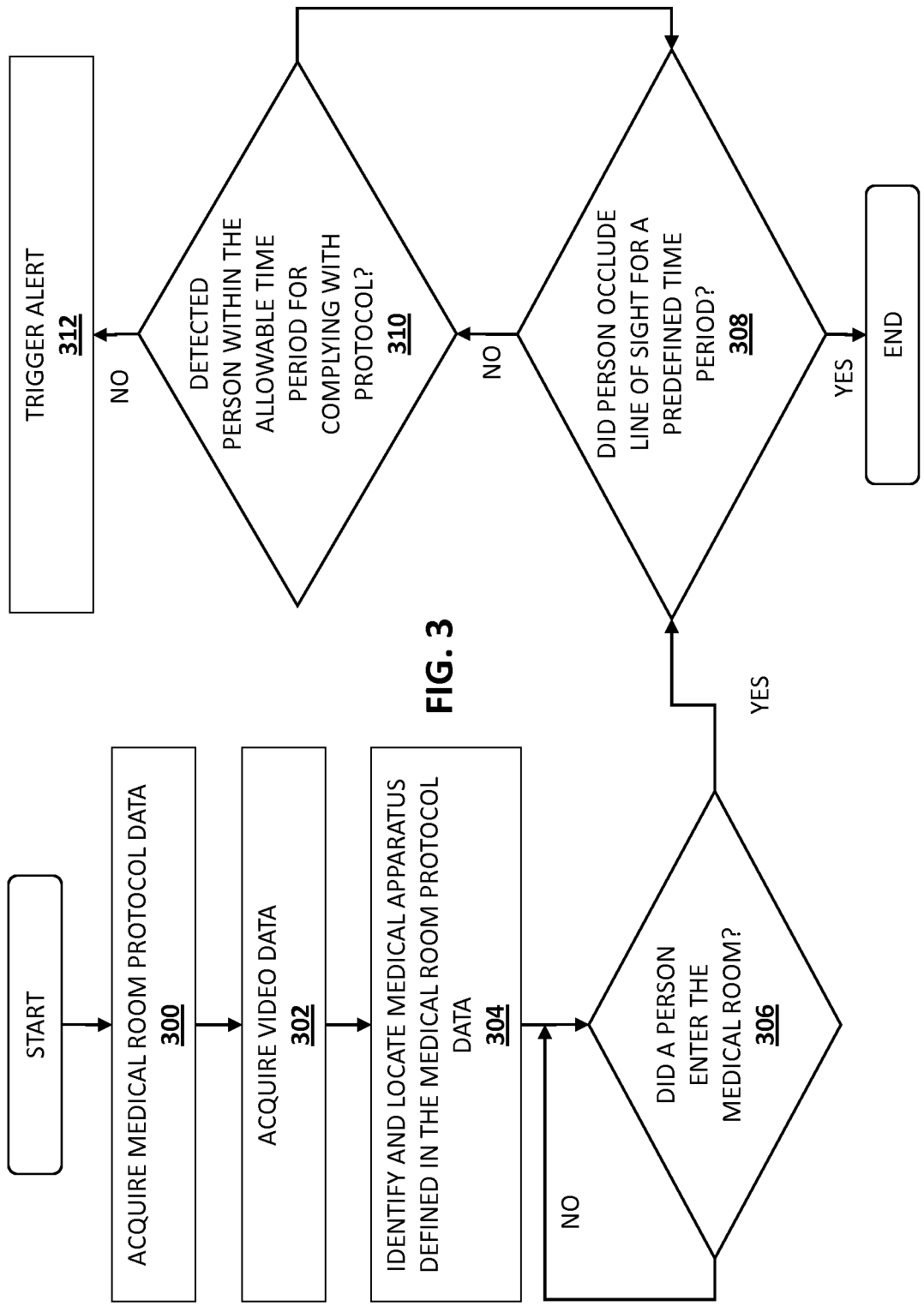
FIG. 3 illustrates an example embodiment of the system of the present disclosure.

FIG. 3 illustrates a flowchart according to another embodiment of the present disclosure. The image monitoring device 100 accesses the computing device 112 via the communications module 106. At block 300, the image monitoring device 100 may acquire medical room protocol data from the medical room protocol database 114. In some embodiments, medical room protocol data may include a protocol, a medical apparatus used for the protocol, and a time period corresponding to the minimum time required for a healthcare provider to accomplish the protocol. Medical room protocol data may also include an allowable time period for the healthcare provider to comply with the protocol. In some embodiments, the medical room protocol data may also include a schedule for the performance of the medical protocol, e.g., a cleaning protocol in which a healthcare provider must sanitize medical instruments is scheduled prior to a scheduled surgery.

After acquiring medical room protocol data at block 300, at block 302 the image monitoring device 100 may acquire video data. The video data may be fed electronically in digital or analog format to the logic 104. The logic 104 may be configured to perform various types of image processing in order to detect and identify people or objects based on the video data. By performing image processing on the video data at block 304, a medical apparatus specified in the medical room protocol data may be located in the medical room. For example, in some embodiments, the image processing may include object recognition to identify the medical apparatus based on records in object database 130. As another example, in some embodiments, the image processing may include recognition of visual indicia such as bar codes or quick response codes that are affixed to surfaces of medical apparatus. In an alternative embodiment, the medical apparatus and its location may be pre-stored in the memory 108 of the image monitoring device 100. In another alternative embodiment, instead of determining and locating a medical apparatus, the image monitoring device 100 may detect a predefined area or region within its field of view wherein a medical protocol is scheduled to be performed.

At block 306 (which may or may not occur simultaneously with the operation of block 302), the image monitoring device 100 may continuously detect if a person has entered the medical room via image processing. A person that enters the medical room may be identified using video data acquired by the image sensor 102. In some embodiments, an identifying marker or indicia such as a bar code, quick response code, etc., may be affixed to apparel worn by a healthcare provider, and may be detected by the image sensor 102. The barcode may provide, for instance, information of the healthcare provider's complete name, department and/or position. In other embodiments, textual markings (e.g., a name and/or title) affixed to apparel worn by the medical provider may be detected, e.g., using optical character recognition.

At block 308, the image monitoring device 100 may determine whether the person detected at block 306 occludes a monitoring device line of sight to the determined medical apparatus. To avoid false detection of the detected person performing the protocol, the occlusion of the monitoring device line of sight to the determined at least one medical apparatus must last for a period of time defined in the medical protocol data. Thus, detection of occlusion for a preset period of time by the detected person of the monitoring device line of sight to the determined medical apparatus indicates that the detected person has complied with the medical room protocol.

If at block 308 the detected person occludes the monitoring device line of sight to the determined medical apparatus for a predefined time period, the process may end. Otherwise, at block 310, the system may determine if the detected person is still within the maximum time threshold for complying with the protocol as defined in the medical protocol data. If so, the process may loop back to block 308, at which a determination is made whether the detected person occludes the monitoring device line of sight to the determined medical apparatus for a predefined time period. On the other hand, if the answer at block 310 is no (e.g., the detected person exceeds the allowable time period for complying with the protocol), then at block 312, an alert may be triggered, e.g., via the alert system 116. In various embodiments, the alert system 116 may provide an auditory and visual alert to the healthcare provider within the room. Additionally or alternatively, the alert system 116 may send a notification to a facility staff regarding the non-compliance of the healthcare provider with the scheduled medical room protocol.

Figure 4:
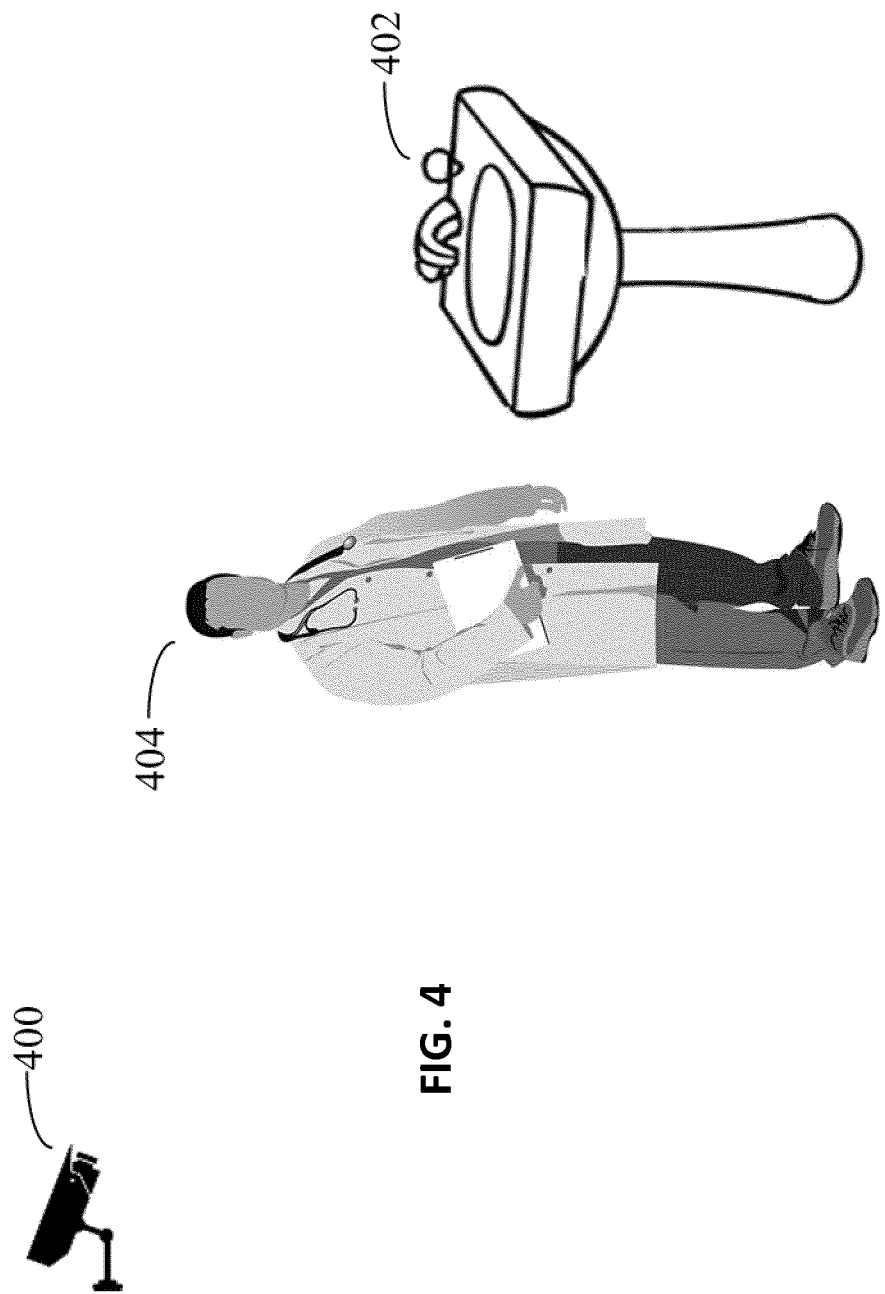
FIG. 4 illustrates a flowchart according to an embodiment of the present disclosure.

FIG. 4 illustrates an example embodiment of the system of the present disclosure. Hospitals have protocols that require surgeons to scrub their hands and arms prior to entering the operating room, the required scrubbing being typically done for a minimum of at least three minutes. Suppose a video camera 400 shown in FIG. 4 is programmed to detect the compliance of a surgeon with the aforementioned scrubbing protocol within some predetermined time interval (e.g., twenty minutes) from the surgeon's entry into the room. The detection of the compliance of a surgeon with the scrubbing protocol may be performed by detecting occlusions of the line of sight of the video camera 400 to a sink 402. The video camera 400 may be configured to disregard any occlusions that lasts for less than three minutes.

As shown in FIG. 4, a video camera 400 is strategically positioned inside a surgery prep room, wherein a sink 402 is within its line of sight. The surgeon 404 enters the surgery prep room to prepare for a scheduled operation on a patient. The video camera 400 detects and identifies the surgeon 404. The following paragraphs will discuss different possible embodiments of the disclosure illustrating how the system works after detection of the doctor's entry into the room.

In a first example, the surgeon 404 complies with the scrubbing protocol. In this case, the surgeon 404 blocks the view of the video camera 400 to the sink 402 while scrubbing. The video camera 400 detects the occlusion of its line of sight to the sink 402. It also detects that the occlusion lasted for three minutes. As a result, the video camera 400 determines that the surgeon 404 has complied with the scrubbing protocol and terminates the program.

A second scenario is one in which the surgeon 404 does not comply with the scrubbing protocol. Suppose the surgeon 404 did not use the sink 402 and therefore did not occlude the line of sight of the video camera 400 to the sink 402. Once the surgeon 404 entered the surgery prep room and was detected by the video camera 400, the surgeon 404 may only be allowed twenty minutes to comply with the protocol. In this case, the video camera 400 did not detect an occlusion to its line of sight to the sink 402 for twenty minutes after the surgeon 404 entered. Accordingly, various alerts, such as a sound alarm, may then be then triggered to alert the surgeon 404 of non-compliance with the protocol.

A third scenario is one in which the surgeon 404 does not comply with the scrubbing protocol but causes an occlusion to the line of sight of the video camera 400 to the sink 402. Suppose the surgeon 404 scrubs for less than the required scrubbing period. In these cases, the video camera 400 detects the occlusion. But because the surgeon failed to comply with the scrubbing period, the surgeon left the line of sight early, and thus the occlusion lasted for less than the required three minutes. In some embodiments, the video camera 400 may disregard such an occlusion and continue to determine if the surgeon 404 complies with the scrubbing protocol up to the allowed twenty minute-period for compliance.

Figure 5:
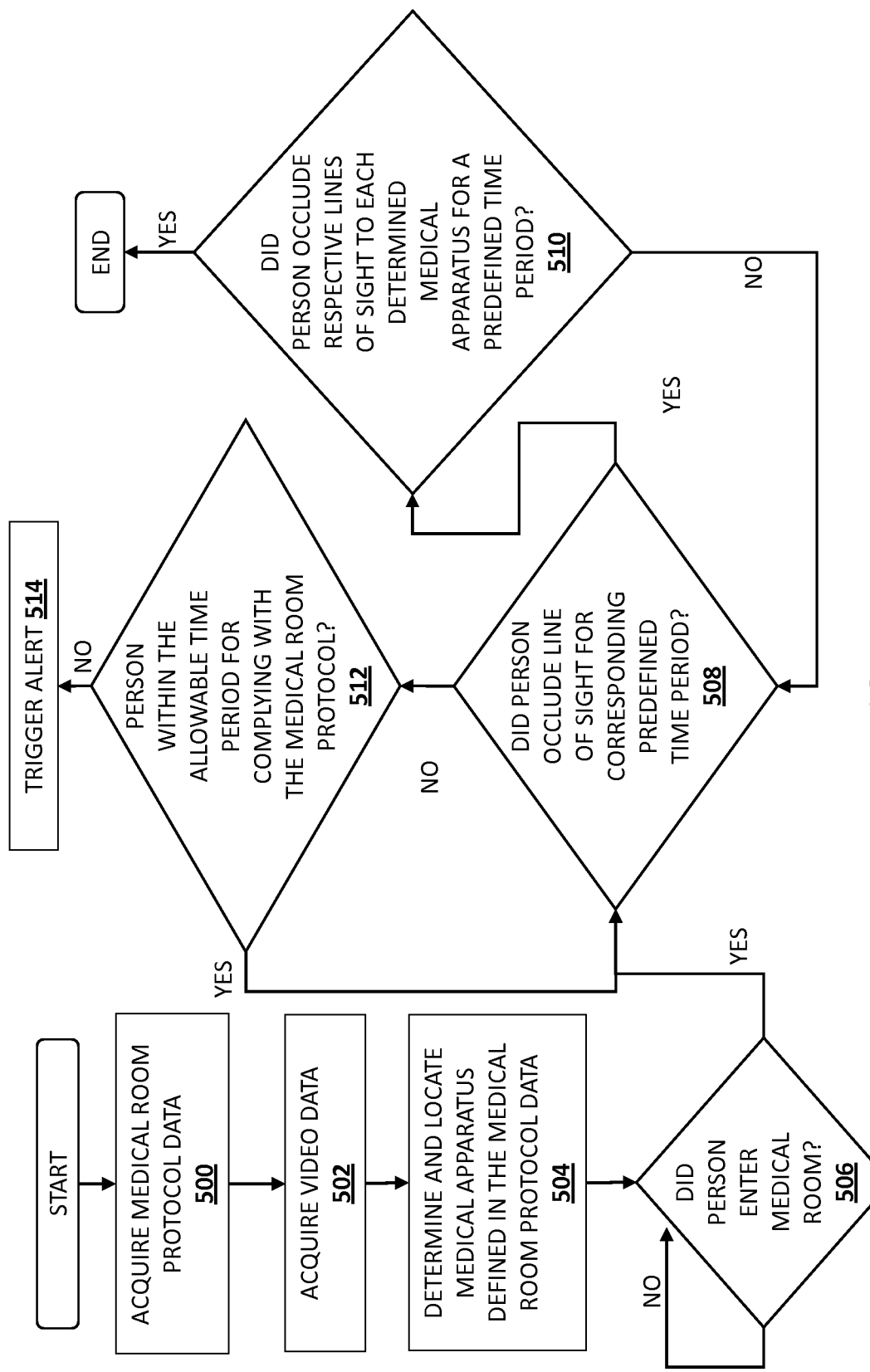
FIG. 5 illustrates a flowchart according to another embodiment of the present disclosure in which the detected health care provider has to comply with multiple medical room protocols.

FIG. 5 illustrates a flowchart according to another embodiment of the present disclosure. A healthcare provider may have to comply with a plurality of protocols, each of which pertains to a different medical apparatus. For example, between scheduled operations, a nurse must prepare and sterilize the operating table and the equipment to be used for the operation. In such a case, the process shown in FIG. 5 is followed.

At block 500, the image monitoring device 100 may acquire medical room protocol data from the medical room protocol database 114 via the communications module 106. At block 502, the image monitoring device 100 may acquire video data. At block 504, all medical apparatus defined in the medical room protocol data may be determined and located in the medical room, e.g., by performing image processing on the video data acquired at block 502. At block 506 (and in some embodiments, simultaneous to the acquisition of video data at block 502), the image monitoring device 100 may continuously loop to determine if a person has entered the medical room. Once the system detects and identifies the person that enters the medical room at block 506, the method may proceed to block 508.

At block 508, the system may determine whether the detected person occludes the monitoring device line of sight to one of the determined medical apparatus for a corresponding time period defined in the medical protocol data. If the answer at block 508 is yes, then at block 510, the system may determine if all protocols have been complied with by the detected person. For example, the system may determine whether the respective lines of sight of the image monitoring device 100 to each of the determined medical apparatus has been occluded for a predefined time period. If the answer at block 510 is yes, the process ends. If the answer at block 510 is no, the system may loop back to block 508, a medical protocols pertaining to additional medical apparatus may be checked.

Back at block 508, if the detected person does not occlude the monitoring device line of sight to one of the determined medical apparatus for a corresponding predefined time period, the method may proceed to block 512. At block 512, the system may determine if the detected person is within the allowable period for complying with the protocol as defined in the medical protocol data. If the answer at block 512 is yes, then the method may loop back to step 508. If the detected person exceeds the allowable time period for complying with the protocol, then at block 514, an alert may be triggered, e.g., via the alert system 116.

FIG. 6 illustrates a flowchart according to yet another embodiment of the present disclosure. In this example, a healthcare provider is required to comply with one or more protocols. In the case of multiple protocols, the protocols may be performed in a specific sequence wherein each protocol in the sequence utilizes a medical apparatus. For example, suppose a surgeon must perform scrubbing prior to an operation. Immediately thereafter, the surgeon must wear the appropriate gear, such as a surgical gown, a surgical cap, a surgical mask, and gloves. In such a case, the process shown in FIG. 6 may be followed.

At block 600, the image monitoring device 100 may acquire medical room protocol data from the medical room protocol database 114 via the communications module 106. At block 602, the image monitoring device 100 may acquire video data. At block 604 (and in some instances, simultaneous to the acquisition of video data at block 602), the image monitoring device 100 may continuously loop to determine if a person has entered the medical room.

Once the system detects and identifies a person that enters the medical room at block 604, at block 606, the medical apparatus utilized in the first protocol as defined in the medical room protocol data may be identified and located in the medical room, e.g., by performing image processing of the video data acquired at block 602. At block 608, the system may determine whether an occlusion caused by the detected person of the monitoring device line of sight to the determined medical apparatus lasted for a predefined time period. If the answer is yes, at block 610, the system may then determine whether the detected person has complied with all the protocols in the sequence. If the answer at block 610 is yes, the process may end. If the answer at block 610 is no, the system may then proceed to the next protocol in the sequence at block 612, and may loop back to block 606 to determine and locate the medical apparatus utilized in the next protocol in the sequence.

Back at block 608, if the detected person does not occlude the monitoring device line of sight to the determined medical apparatus for a predefined time period, then at block 614, the system may determine if the detected person still has time within the allowable time interval for complying with the protocol as defined in the medical protocol data. If the answer at block 614 is yes, the system may loop back to block 608. If the answer at block 614 is no (e.g., the detected person cannot comply with the protocol within the allowed time interval), at block 616, an alert may be triggered, e.g., via the alert system 116.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

The present disclosure is not intended to be restricted to the several exemplary embodiments of the disclosure described above. Other variations that may be envisioned by those skilled in the art are intended to fall within the disclosure.

The invention claimed is:

1. A computer-implemented method, comprising:
    acquiring, using a single image sensor, video data that captures a medical room;
    performing, using an image monitoring device including an image input and one or more processors, image processing on the acquired video data to determine whether it is possible that a medical personnel has complied with a first medical protocol, wherein the image processing includes:
        identifying at least one medical apparatus in the medical room in a line of sight with the image monitoring device;
        identifying a medical personnel in the medical room;
        detecting that the medical personnel has occluded the line of sight between the image monitoring device and the at least one medical apparatus; and
        determining an amount of time that the medical personnel occludes the line of sight;
    comparing the amount of time that the medical personnel occludes the line of sight to a first predefined time period corresponding to a minimum time required to avoid a false detection;
    comparing the amount of time that the medical personnel occludes the line of sight to a second predefined time period corresponding to a minimum time required for a medical personnel to accomplish the first medical protocol;
    disregarding the amount of time that the medical personnel occludes the line of sight when the amount of time that the medical personnel occludes the line of sight is less than the first predefined time period; and
    triggering an alert in response to a determination that the amount of time that the medical personnel occludes the line of sight is less than the second predefined time period.

2. The computer-implemented method of claim 1, further comprising performing imaging processing on the acquired video data to determine an amount of time the medical personnel has been in the medical room.

3. The computer-implemented method of claim 2, wherein the step of triggering the alert comprises only triggering the alert in response to a determination that the amount of time the medical personnel has been in the medical room exceeds a predetermined allowable time period for the medical personnel to comply with the first medical protocol after entry into the medical room, wherein the predetermined allowable time period is greater than the second predefined time period corresponding to the minimum time period required for the medical personnel to accomplish the first medical protocol.

4. The computer-implemented method of claim 1, wherein identifying the at least one medical apparatus in the medical room comprises performing object recognition on the acquired video data.

5. The computer-implemented method of claim 1, wherein identifying the at least one medical apparatus in the medical room comprises detecting visual indicia affixed to a surface of the at least one medical apparatus.

6. The computer-implemented method of claim 1, wherein identifying the medical personnel in the room comprises detecting visual indicia worn by the medical personnel, wherein the visual indicia comprises a bar code or quick response code.

7. The computer-implemented method of claim 1, wherein identifying the medical personnel in the room comprises performing optical character recognition to read at least one textual marking worn by the medical personnel.

8. The computer-implemented method of claim 1, wherein identifying the medical personnel in the room comprises performing facial recognition to identify the medical personnel.

9. A system for reinforcing medical room protocols comprising:
    a medical room protocol database that stores medical room protocols comprising a first medical protocol;
    an image monitoring device comprising an image input arranged to receive, by a single image sensor, acquired video data that captures a medical room, and one or more processors to perform image processing on the acquired video data to:
        identify at least one medical apparatus in the medical room in a line of sight with the image monitoring device;
        identify a medical personnel in the medical room;
        detect that the medical personnel has occluded the line of sight between the image monitoring device and the at least one medical apparatus;
        determine an amount of time that the medical personnel occludes the line of sight;
        compare the amount of time that the medical personnel occludes the line of sight to a first predefined time period corresponding to a minimum time required to avoid a false detection; and
        disregard the amount of time that the medical personnel occludes the line of sight when the amount of time that the medical personnel occludes the line of sight is less than the first predefined time period; and
    an alert system comprising one or more processors for triggering an alert when the medical personnel occludes a line of sight between the image monitoring device and the at least one medical apparatus for an amount of time that is more than the first predefined time period and less than a second predefined time period corresponding to a minimum time required for a medical personnel to accomplish the first medical protocol.

10. The system of claim 9, wherein the image monitoring device is further arranged to perform imaging processing on the received video data to determine an amount of time the medical personnel has been in the medical room.

11. The system of claim 10, wherein the alert system triggers the alert further in response to a determination that the amount of time the medical personnel has been in the medical room exceeds a predetermined allowable time period for the medical personnel to comply with the first medical protocol after entry into the medical room, wherein the predetermined allowable time period is greater than the second predefined time period corresponding to the minimum time period required for the medical personnel to accomplish the first medical protocol.

12. The system of claim 10, wherein identifying the at least one medical apparatus in the medical room comprises performing object recognition on the acquired video data.

13. The system of claim 10, wherein identifying the at least one medical apparatus in the medical room comprises detecting visual indicia affixed to a surface of the at least one medical apparatus.

14. The system of claim 10, wherein identifying the medical personnel in the room comprises detecting visual indicia worn by the medical personnel, wherein the visual indicia comprises a bar code or quick response code.

* * * * *